Figure 1:
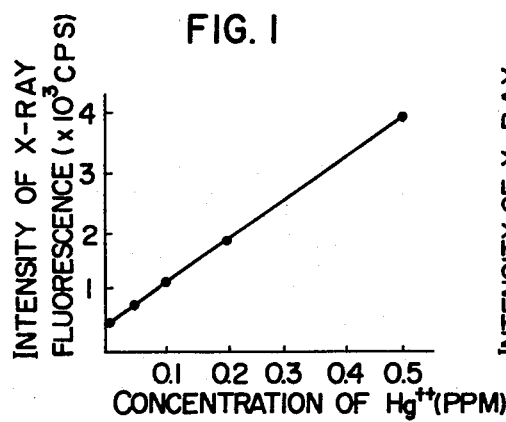

United States Patent [19]

Sano et al.

[11] 4,080,171

[45] Mar. 21, 1978

[54] RAPID ANALYSIS OF TRACE COMPONENTS CONTAINED IN A LIQUID

[75] Inventors: Takezo Sano, Takatsuki, Japan; Akira Kobayashi, deceased, late of Ibaraki, Japan; by Shuko Kobayashi, successor; Tsutomu Kobayashi, guardian, both of Kagoshima, Japan

[73] Assignee: Sumitomo Chemical Company, Limited, Osaka, Japan

[21] Appl. No.: 712,695

[22] Filed: Aug. 9, 1976

[30] Foreign Application Priority Data

Aug. 12, 1975 Japan .................... 50-98285

[51] Int. Cl.² .............. B01D 37/02; G01N 21/00; G01N 23/00
[52] U.S. Cl. .................. 23/253 TP; 210/75; 210/193; 210/54; 250/273
[58] Field of Search ........... 23/253 TP; 210/75, 193, 210/54 A, 54 C, 54 R; 162/157 R, 164 R, 158; 250/273

[56] References Cited

U.S. PATENT DOCUMENTS

| | | | |
|---|---|---|---|
| 2,939,814 | 6/1960 | Amphlett et al. | 162/158 R X |
| 2,955,067 | 10/1960 | McBurney et al. | 162/164 R |
| 3,232,867 | 2/1966 | Abrams | 210/75 X |

OTHER PUBLICATIONS

D. G. Biechler, Anal. Chem. 37, 1054 (1965).
Zlatkis et al., Anal. Chem. 41, 1692 (1969).

Primary Examiner—Robert M. Reese
Attorney, Agent, or Firm—Stevens, Davis, Miller & Mosher

[57] ABSTRACT

A method for the rapid analysis of trace components in a liquid, which comprises filtering said liquid through a filter paper having at least one of anion exchange functional groups and chelating ion binding functional groups, thus collecting substantially the entire amount of the objective components (anions or chelating ions) contained in said liquid on the filter paper, and analyzing the anion- or chelating ion-loaded filter paper as such or after drying, or analyzing the eluate obtained by elution of the anions or chelating ions to be analyzed from said filter paper.

11 Claims, 4 Drawing Figures

RAPID ANALYSIS OF TRACE COMPONENTS CONTAINED IN A LIQUID

The present invention relates to a method for collecting objective components on a filter paper having a functional group and analyzing them rapidly.

In recent years, in connection with waste water analysis, water quality control and analysis of valuable trace components, the need for sensitive and rapid analytical methods has become increasingly great. With the progress in the development of various analytical instruments, the accuracy of analysis has been improved more and more. However, the pre-treatment of a test sample is complicated and requires much labor so that the analytical operation lacks rapidity. The inventors studied to improve those defects and found a rapid method of the analysis of metals by means of a cation exchange filter paper. Further, the inventors have continued a detailed study of this method and found that it is applicable more widely.

An object of the present invention is to provide a rapid method for the analysis of anions or chelating ions which are contained in a liquid as a trace component.

The present invention is characterized by filtering a liquid through a filter paper having at least one of anion exchange functional groups and chelating ion binding functional groups, thus collecting substantially the entire amount of the objective components (anions or chelating ions) contained in said liquid on the filter paper, and analyzing the anion- or chelating ion-loaded filter paper as such or after drying, or analyzing the eluate obtained by elution of the anions or chelating ions to be analyzed from said filter paper.

The filter paper used in the present invention should have at least one of anion exchange functional groups and chelating ion binding functional groups and at the same time the ion exchange capacity of the filter paper is preferably 0.1 to 10 meq/g. Further, it is desirable that the filter paper be resistant to solvents and have a high enough strength to withstand the filtration procedure and a high dimensional stability. A suitable water permeability of the filter paper is about 1 to about 1,000 seconds, and preferably 5 to 100 seconds, in terms of filtration time required for 1 cc of water to be filtered through 1 cm$^2$ of filter paper under a water head of 10 cm.

As the anion exchange functional groups used, there are generally exemplified primary, secondary and tertiary amino groups, quaternary ammonium group and groups containing a pyridine nucleus or pyridinium nucleus.

The chelating ion binding functional groups may be any of those which form a strong bond with metals selectively. Specifically, they include thiourea, phenylthiourea, thiosemicarbazide, thiocarbazide, dithiocarbamate, dithiocarbamic acid, dithioic acid, thiol, polythiol, acetamino, iminodiacetato, o-aminophenol, ethylenediamino, polyethylenepolyamine and resorcinol groups.

The thickness of the filter paper is preferably about 0.1 to 5 mm. The shape, thickness and surface area of the filter paper may suitably be determined depending upon the analytical means.

The present filter paper can be made in several ways, but a particularly preferred method among them is the one comprising introducing the functional groups into natural or synthetic pulp and making paper from the pulp, if necessary, together with a binding agent. In this case, fibril-form pulp of 0.5 to 100 μ in diameter is desirable. When the functional groups are introduced into such a pulp and filter paper is then made from the pulp, the filter paper obtained has a sufficient strength and an extremely high rate of ion exchange and chelating ion binding which are suitable for the method of the present invention. The pulp used as a starting material includes synthetic pulp, for example, polyethylene pulp, polypropylene pulp, polystyrene pulp and polyvinyl chloride pulp, and cellulosic natural pulp. If necessary, introduction of the functional groups may be carried out as follows: Reactive groups such as chlorine atom or chloromethyl group are first introduced into pulp and the functional groups are then introduced. In making the filter paper from a pulp, other kinds of pulp may be blended to control the strength of the filter paper. At least two kinds of pulp having the functional groups may be blended in order to make the filter paper having a wide range of application.

The analytical method of the present invention may be applied to any sample in the form of liquid such as an aqueous solution or a solution in organic solvents. The sample may contain a suspended solid or an emulsified matter.

The components analyzable by the method of the present invention depend, of course, upon the kind of functional groups introduced into the filter paper. By proper selection of functional groups, the following anions can be analyzed: Anions of oxoacids such as aluminic acid, chromic acid, silicic acid, boric acid, sulfuric acid, sulfurous acid, thiosulfuric acid, carbonic acid, phosphoric acid, arsenic acid, arsenous acid, thiocyanic acid, hypochlorous acid, chloric acid, nitrous acid and nitric acid; anions of halogens such as fluorine, chlorine, bromine and iodine; complex anions such as ferricyanide ion, ferrocyanide ion and chloroplatinate ion; anions of organic acids such as acetic acid, oxalic acid, formic acid, tartaric acid, organosulfonic acids and organophosphoric acids, and cyanide ion.

The chelating ion binding functional groups have strong selectivity toward a metal so that they can be used for a selective analysis. This property is very useful for the analysis of poisonous heavy metals which are present together with a large amount of non-poisonous ions, as is often encountered in common waste water. Possible examples of a combination of a metal and a functional group are as follows: dithiocarbamic acid group for the analysis of mercury, gold, silver and chrome; an iminodiacetato group for copper, zinc, calcium, cadmium, mercury, lead, manganese and nickel; a dithioic acid group for gold, silver and mercury; and an ethylenediamino group for mercury, gold, silver, chrome, nickel, copper, zinc and cadmium.

For example, saving in the time and labor required for analysis can be attained by placing at least two kinds of filter paper having different selectivities one upon another, and filtering a liquid through the layers of filter paper only once to catch the metals in the liquid fractionally by the respective filter papers, followed by analysis. When the liquid contains insoluble materials, they are also collected on the filter paper by the filtration, and then analyzed at the same time.

The filtration method will be illustrated specifically. First, a filter paper is properly selected depending upon the kind of components to be analyzed. The paper is mounted on a filter holder or placed on a Buechner funnel and the liquid sample is passed through the filter paper at a space velocity [a linear velocity (cm/hr)/thickness (cm)] of 1 to 10,000 hr$^{-1}$, and preferably 10 to 1,000 hr$^{-1}$, to collect the objective components. When the liquid sample contains unnecessary suspended matters, they are preferably removed by filtering the liquid sample through common filter paper having no functional groups which is placed on the above-described filter paper.

The components collected on the filter paper can be analyzed by the following techniques:

(1) Elementary analysis after drying.

(2) X-ray fluorescence analysis of the components as collected on the filter paper without drying or after drying.

(3) Emission spectroscopic analysis after drying. (4) Measurement of radioactivity of the components as collected on the filter paper (trace analysis of radioactive constituent).

(5) Radio activation analysis after drying.

(6) Reflective infrared analysis after drying.

(7) Atomic absorption analysis after elution.

(8) Polarography after elution.

(9) Visible and ultraviolet spectroscopic analysis after elution.

(10) Polarimetry after elution.

(11) Nuclear magnetic resonance spectral analysis after elution.

Other combinations than those mentioned above are also possible. Of the above-mentioned analytical techniques, those of (2), (5), (7) and (8) are superior in sensitivity and rapidity of the analysis and particularly the techniques (2) and (7) are very useful and will become an important analytical technique in the future.

The advantages of the present method may be summarized as follows: First, owing to a markedly high rate of ion exchange and chelating ion binding of the filter papers, the objective components present in trace amounts in a large volume of a liquid can be collected rapidly and completely. Secondly, the method of the present invention can be applied to a wide range of test samples by the selection of the filter papers. Thirdly, since the filter paper of the present invention has a high ability to catch the objective components on the surface thereof, the anion-loaded filter paper can be analyzed as it is by the X-ray fluorescence analysis and reflective infrared analysis. Consequently, simplicity and rapidity are particularly superior. Fourthly, since the objective components can immediately be collected by filtration on the sampling spot, it becomes possible to save the time and labor required to carry a large quantity of the liquid to an analytical laboratory. Fifthly, it is possible to collect heavy metals along selectively by the use of chelating ion binding filter paper from sea water and river water having a high salt concentration and to analyze them rapidly. Sixthly, in X-ray fluorescence analysis, it is possible to fractionate and analyze multicomponent ions simultaneously with high sensitivity and rapidity.

The present invention will be illustrated in detail with reference to the following examples, but the invention is not limited to those examples.

Figure 2:
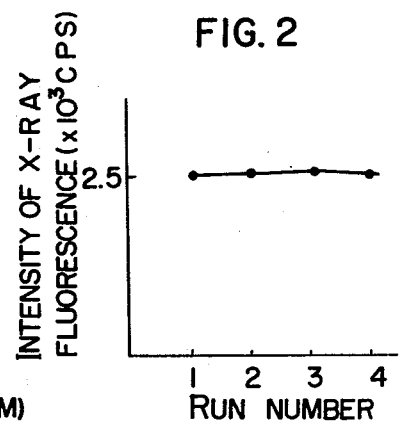
Figure 3:
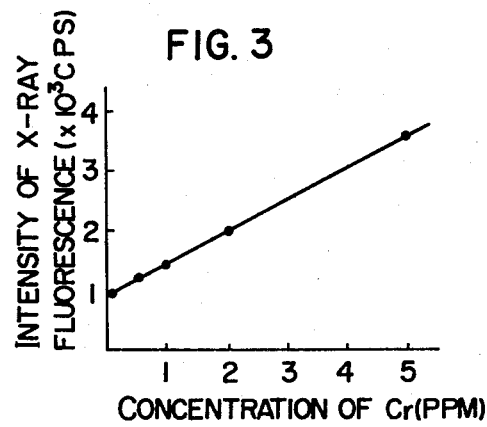
Figure 4:
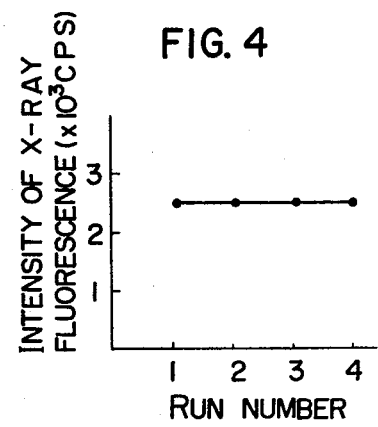

The accompanying drawings show the experimental results of the examples described hereinafter. FIG. 1 shows the relationship between mercury concentrations and counts of fluorescent X-rays in Example 1. FIG. 2 shows the reproducibility of the analytical method in Example 1 at a definite mercury concentration. FIG. 3 shows the relationship between Cr (chrome) concentrations and counts of fluorescent X-rays in Example 3. FIG. 4 shows the reproducibility of the analytical method in Example 3 at a definite concentration of Cr.

EXAMPLE 1

Polyvinyl chloride fiber (2-denier) was chopped to a length of 5 to 10 mm. To 10 parts by weight of the chopped fiber were added 60 parts by weight of ethylenediamine and 15 parts by weight of water. The resulting mixture was reacted at 110° C for 6 hours. The reaction product was filtered, washed with water and dried to obtain 8.1 parts by weight of a yellowish brown aminated polyvinyl chloride fiber (hereinafter referred to as "Fiber I").

To 10 parts by weight of the Fiber I was added 25 parts by weight of carbon disulfide. The mixture was reacted at 40° C for 3 hours. The reaction product was filtered, washed with water and dried to obtain 13.1 parts by weight of a fiber containing a dithiocarbamic acid group (hereinafter referred to as "Fiber II").

A filter paper of 1 mm in thickness (basis weight 350 g/m$^2$) was produced by blending 10 parts by weight of the Fiber II with 3 parts by weight of natural cellulose pulp in water according to a usual method for making paper.

Through the thus obtained chelating ion binding filter paper, 47 mm in diameter, containing a dithiocarbamic acid group (ion exchange capacity 5 meq/g), 100 ml each of aqueous solutions having different Hg$^{++}$ concentrations, 0.01, 0.05, 0.1, 0.2 and 0.5 ppm, was passed, over 10 minutes, whereby Hg$^{++}$ ions were caught by the filter paper. Each filter paper was dried and measured for the counts of fluorescent X-rays (Geigerflux SX of Rigaku Denki Co., Ltd.). As shown in FIG. 1, a good linear relationship was found between mercury concentrations and the counts. The reproducibility of the analytical method was examined using the aqueous solution having a Hg$^{++}$ concentration of 0.3 ppm. The good results were obtained as shown in FIG. 2. The filtrate obtained by passing the Hg$^{++}$- containing aqueous solution through the chelating ion binding filter paper was analyzed for Hg$^{++}$ ions by an atomic absorption analysis. However, Hg$^{++}$ ion was not detected at all.

EXAMPLE 2

100 Milliliters each of simulated waste waters containing 2.7% of sodium chloride and having different concentrations of Hg$^{++}$, 0.02, 0.08, 0.1 and 0.3 ppm, was passed through the same filter paper as in Example 1 under the same conditions as in Example 1. Each of the Hg$^{++}$ ion-loaded filter papers was analyzed according to the same procedure as in Example 1. Thus, the same good linear relationship as in FIG. 1 was found between mercury concentrations and the counts of fluorescent X-rays. The time required for the analysis was about 2 hours.

EXAMPLE 3

100 Milliliters each of aqueous solutions having different concentrations of CrO$_4^-$, 0.1, 0.5, 1, 2 and 5 ppm (converted to Cr basis), was passed through a strongly basic ion exchange filter paper of 47 mm in diameter and 0.25 mm in thickness (ECTEOLA© produced by Toyo Roshi Co., Ltd.), in the same manner as in Example 1. The anion-loaded filter paper was subjected to the X-ray fluorescence analysis. As a result, a good linear relationship between Cr concentrations and intensities of fluorescent X-ray and a good reproducibility of the analytical method were obtained as shown in FIGS. 3 and 4. Further, Cr ion in the filtrate was not detected as in Example 1.

EXAMPLE 4

10 Liters of an aqueous solution containing 0.1 ppm of $BO_2^-$ ion were passed, over 1 hour, through five sheets of the same ion exchange filter paper as in Example 3 which were placed one upon another. Thus, the $BO_2^-$ ion was caught by the filter paper. The ion was eluted from the paper with 100 ml of 0.1 N sodium hydroxide and subjected to common atomic absorption analysis. The error was within 2% and the time required for the analysis was 1.5 hours.

Reference Example 1

10 Liters of the same aqueous $BO_2^-$ solution as in Example 4 were concentrated to 100 ml according to the common evaporation method and subjected to the atomic absorption analysis. The error was within 5% and the time required for the analysis was about 12 hours.

EXAMPLE 5

Polyvinyl chloride fiber (2-denier) was chopped to a length of 5 to 10 mm. To 10 parts by weight of the chopped fiber were added 45 parts by weight of triethylenetetramine and 30 parts by weight of water. The resulting mixture was reacted at 90° C for 10 hours. The reaction product was filtered, washed with water and dried to obtain a yellowish brown aminated polyvinyl chloride fiber. Then, a filter paper of 1 mm in thickness was produced by blending 10 parts by weight of this fiber with 10 parts by weight of natural cellulose pulp in water according to a usual method for making paper.

Through the thus obtained chelating ion binding filter paper, 47 mm in diameter, containing a triethylenetetramine group (ion exchange capacity 3 meq/g), 10l of an aqueous solution containing 1 ppm of $Cu^{++}$ ion were passed over 1 hour. Thus the $Cu^{++}$ ion was caught by the filter paper. The ion was eluted from the paper with 20 ml of 1N hydrochloric acid and subjected to common polarography. The error was within 2% and the time required for the analysis was about 1.5 hours.

Reference Example 2

10 Liters of the same aqueous $Cu^{++}$ solution as in Example 5 were concentrated to 20 ml by the common evaporation method in order to obtain the same ion concentration of the sample to be analyzed as in Example 5. As the results of polarography, the error was about 10% and the time required for the analysis was about 13 hours.

What is claimed is:

1. A method for the rapid analysis of anions and/or chelating ions contained in a liquid, which comprises filtering a sample of said liquid through a filter paper made from pulp having at least one of anion exchange functional groups and chelating ion binding functional groups, at a space velocity of said liquid sample through said filter paper of 1 to 10,000 $hr^{-1}$ in terms of linear velocity (cm/hr)/thickness (cm), to collect substantially the entire amount of said anions and/or chelating ions contained in the liquid sample on the filter paper, and analyzing said anion- or chelating ion-loaded filter paper.

2. A method according to claim 1, wherein each of the unit fibers composing the filter paper has a diameter of 0.5 to 100 $\mu$.

3. A method according to claim 1 wherein the filter paper containing said functional group is polyethylene, polypropylene, polystyrene, polyvinyl chloride or a cellulose.

4. A method according to claim 1, wherein the anion exchange functional group is a primary, secondary or tertiary amino group, a quaternary ammonium group Or a group containing a pyridine nucleus or pyridinium nucleus.

5. A method according to claim 1, wherein the chelating ion binding functional group is a thiourea, phenylthiourea, thiosemicarbazide, thiocarbazide, dithiocarbamate, dithiocarbamic acid, dithioic acid, thiol, polythiol, acetamino, iminodiacetato, o-aminophenol, ethylenediamino, polyethylenepolyamine or resorcinol group.

6. A method according to claim 1, wherein the filter paper has a thickness of 0.1 to 5 mm.

7. A method according to claim 1, wherein the filter paper has an anion exchange capacity and/or a chelating ion binding capacity of 0.1 to 10 meq/g.

8. A method according to claim 1, wherein the filter paper has a water permeability of 1 to 1,000 seconds, in terms of filtration time required for 1 cc of water to be filtered through 1 $cm^2$ of filter paper under a water head of 10 cm.

9. A method according to claim 1, wherein the analysis of said anion- or chelating ion-loaded filter paper is carried out by measuring the anion or chelating ion on the filter paper by X-ray fluorescence analysis after drying the anion- or chelating ion-loaded filter paper.

10. A method according to claim 1, wherein the space velocity of the liquid sample through the filter paper is 10 to 1,000 $hr^{-1}$.

11. A method according to claim 1, wherein the analysis of the anion- or chelating ion-loaded filter paper is carried out by measuring the anion or chelating ion in the eluate obtained by elution of the objective anion or chelating ion from said anion- or chelating ion-loaded filter paper by means of the method of atomic absorption.

* * * * *